US00PP33113P2

(12) United States Plant Patent
Seaman

(10) Patent No.: US PP33,113 P2
(45) Date of Patent: Jun. 1, 2021

(54) APPLE TREE NAMED 'SO 7'

(50) Latin Name: *Malus domestica*
Varietal Denomination: SO 7

(71) Applicant: Alton R Seaman, Roseland, VA (US)

(72) Inventor: Alton R Seaman, Roseland, VA (US)

(73) Assignee: International Plant Management, Inc, Lawrence, MI (US)

( * ) Notice: Subject to any disclaimer, the term of this patent is extended or adjusted under 35 U.S.C. 154(b) by 0 days.

(21) Appl. No.: 16/873,192

(22) Filed: Feb. 25, 2020

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./156, 161
See application file for complete search history.

*Primary Examiner* — Susan McCormick Ewoldt
*Assistant Examiner* — Karen M Redden

(57) ABSTRACT

A new and distinct variety of 'Honeycrisp' apple tree named 'SO 7' originating as a whole tree mutation. This new variety is unique from its parent in the brighter red, highly colored fruit and bright red coloration of the petiole underside extending to the leaf midvein in a majority of leaves.

3 Drawing Sheets

Latin name of genus and species: *Malus domestica.*

DESCRIPTION OF RELATED APPLICATIONS

The new variety, 'SO 7' differs from its parent and other varieties in the following characteristics:

A. The fruit of the new variety finishes to a bright cherry red color over 80% to 90% of its surface and also exhibits a bright cherry red color over 80% to 90% of its surface and exhibits bright red leaf petiole undersides and mid-vein undersides.

B. The new variety differs from its parent, 'Honeycrisp' (U.S. Plant Pat. No. 7,197) in that it finishes to a bright cherry red color over 80% to 90% of its surface and exhibits bright red leaf petiole undersides and mid-vein undersides.

C. The new variety 'SO 7' differs from 'LJ-1000' (U.S. Plant Pat. No. 22,244) and other related selections in that it exhibits bright red leaf petiole undersides and leaf mid-vein undersides in a majority of leaves. The new variety differs from 'DAS-10' (U.S. Plant Pat. No. 24,833) in that it ripens with the original parent, Honeycrisp.

BACKGROUND OF THE INVENTION

A new and distinct variety of 'SO 7' apple tree originating as a whole tree mutation of the *Malus domestica* variety of 'Honeycrisp', (U.S. Plant Pat. No. 7,197) and is hereinafter referred to as 'SO 7'. This new sport is unique from its parent because the fruit finishes to a bright cherry red color over 80% to 90% of its surface and exhibits bright red leaf petiole undersides and mid-vein undersides.

SUMMARY OF THE INVENTION

This new and distinct variety of 'Honeycrisp' apple tree was discovered in Roseland, Va. as a whole tree mutation of 'Honeycrisp' in an orchard planted in 2009. The new variety was noticed because the fruit started coloring to a much brighter red finish than the surrounding 'Honeycrisp'.

Observations during the next two seasons confirmed that the fruit colored bright cherry red color over 80% to 90% of its surface and exhibited bright red leaf petiole undersides and mid-vein undersides.

In August of 2012, buds were taken from the original tree and trees for further testing were produced by cleft grafting onto existing apple trees. In August of 2014, buds were taken from the original tree and asexually reproduced by chip budding in Brentwood, Calif. The new variety has remained true to the description herein contained. The new variety has not been grown on its own root.

DESCRIPTION OF THE DRAWINGS

The accompanying photographs show typical specimens of the new variety as depicted in color as nearly true as is reasonably possible in color illustrations of this character. These specimens were obtained in Roseland, Va.

NOT A COMMERCIAL WARRANTY

Figure 1:
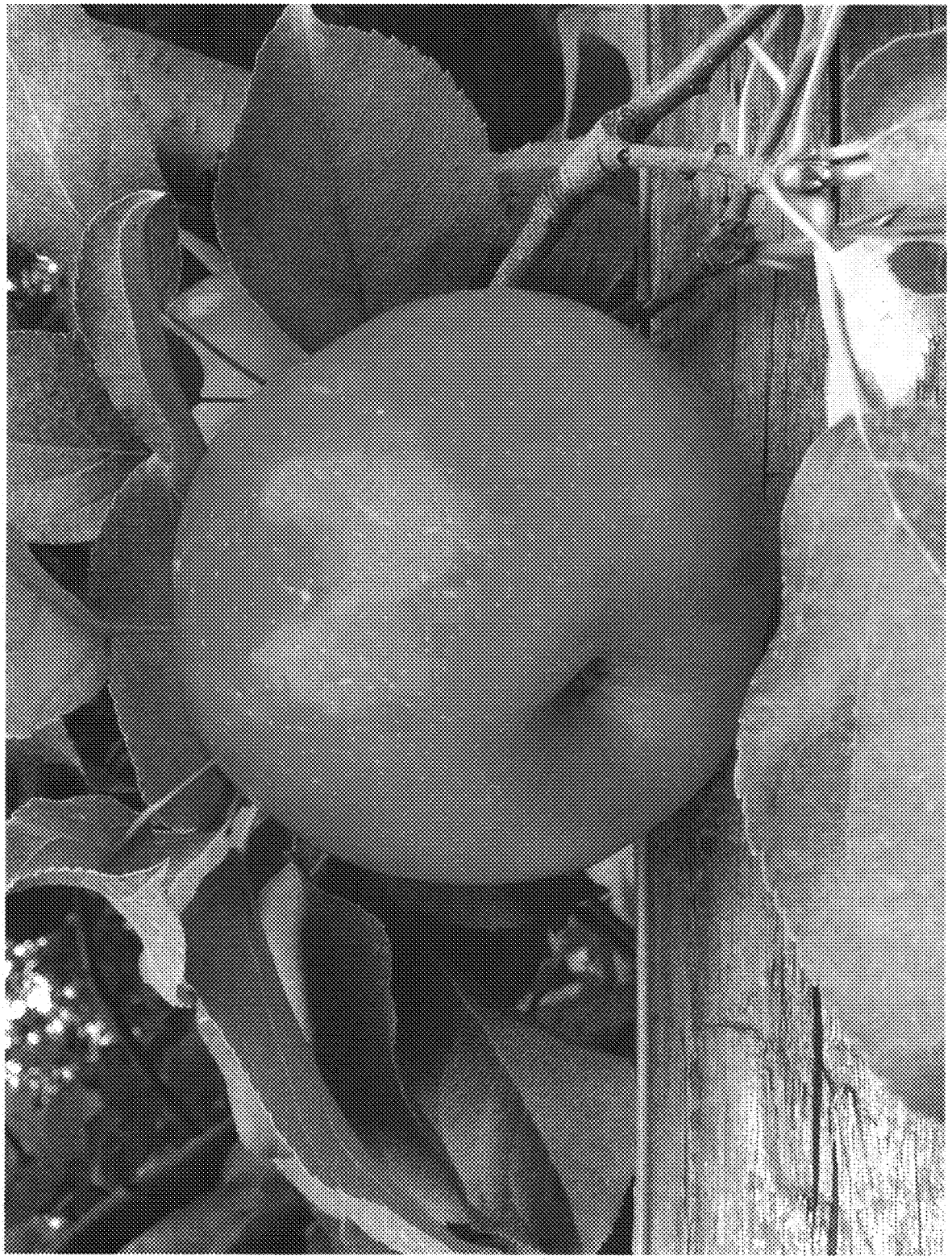
FIG. 1 illustrates the fruits and foliage of the new variety at maturity.
Figure 2:
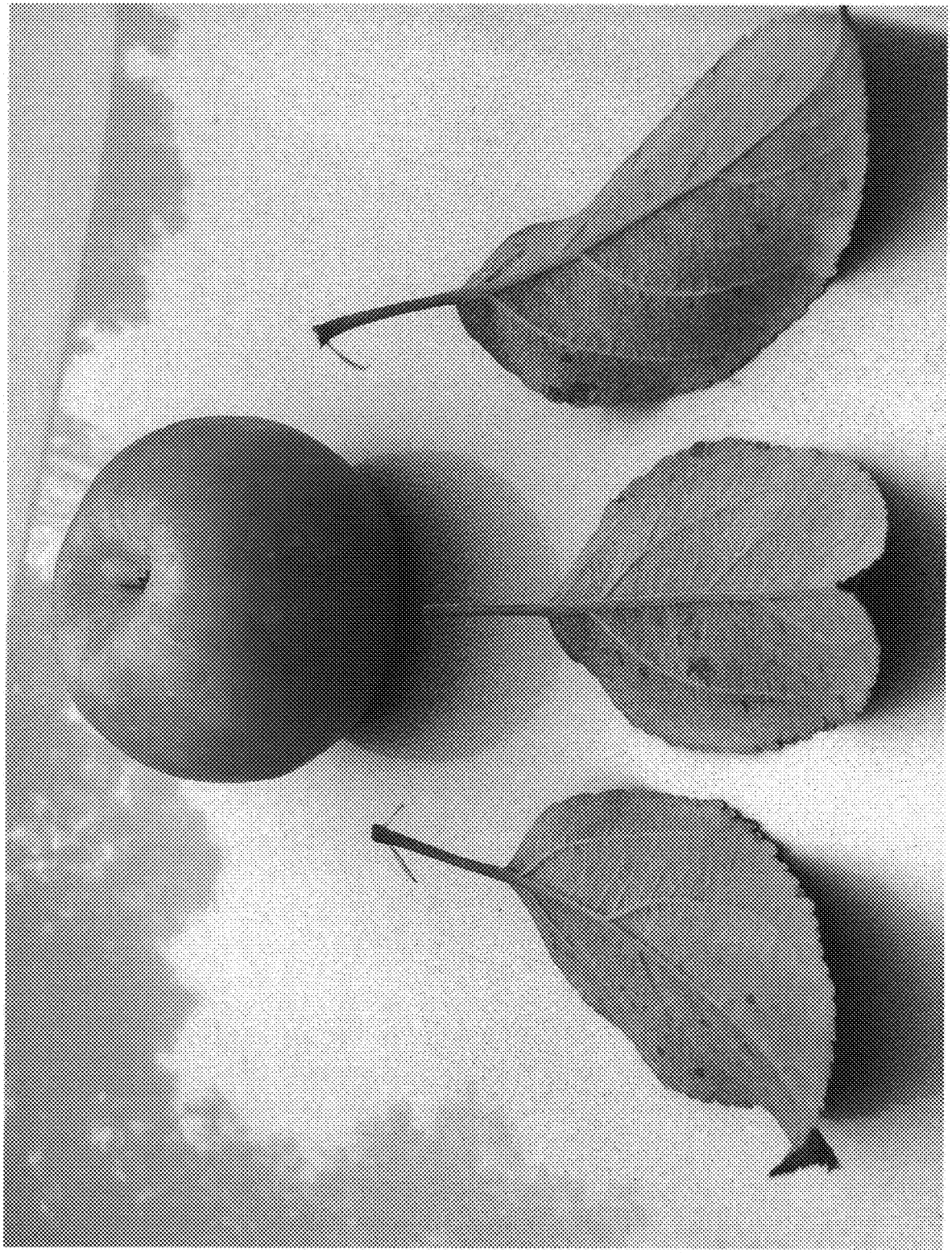
FIG. 2 illustrates a fruit and the underside of the leaves of the new variety.
Figure 3:
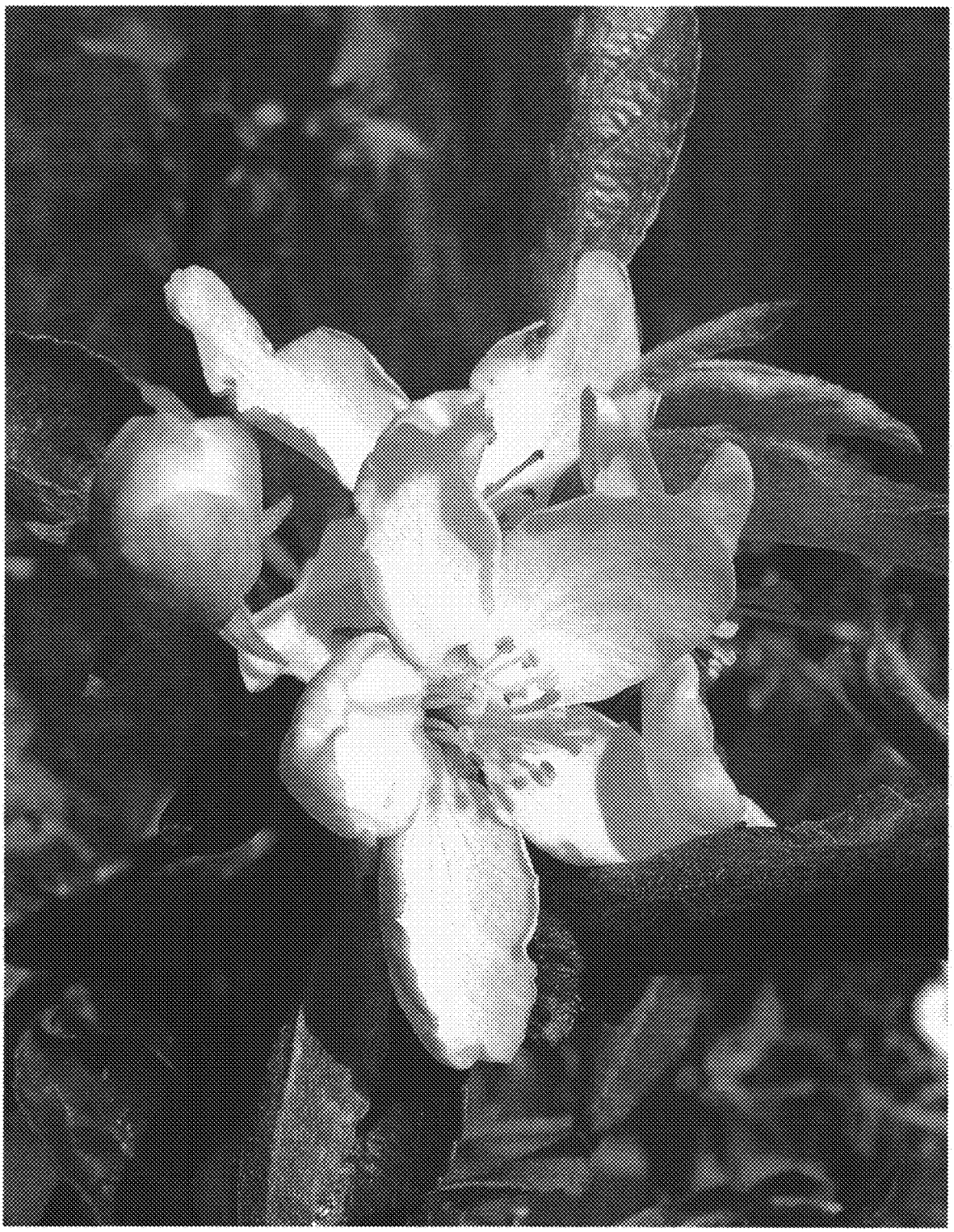
FIG. 3 illustrates blossoms and a bud of the new variety.

The following detailed description has been prepared to solely comply with the provisions of 35 U.S.C. sctn. 112. and does not constitute a commercial warranty, (either expressed or implied), that the present variety will, in the future, display the botanical, pomological or other characteristics as set forth, hereinafter. Therefore, this disclosure may not be relied upon to support any future legal claims including, without limitation, any claims relating to the breach of warranty of merchantability, or fitness for any particular purpose, or non-infringement which is directed, in whole, or in part, to the present variety.

DETAILED BOTANICAL DESCRIPTION

A detailed description of the 'SO 7' cultivar follows using The Royal Horticultural Society of London Colour Chart, 1986 edition, for color identification except where general color terms are sufficient.

Parentage: A whole tree mutation of 'Honeycrisp' (U.S. Plant Pat. No. 7,197). Locality of the original discovery and observations is Roseland, Va.

Tree:
- *Age.*—10 years.
- *Size.*—medium, height 3 m, width 3 m.
- *Vigor.*—Medium, yearly growth averages 0.5 m.
- *Density.*—Open.
- *Form.*—Wide.
- *Production.*—Medium to heavy, averaging 2 bushels to 3 bushels per tree dependent on the dwarfing rootstock used.
- *Growth type.*—Spreading.
- *Bearing.*—Annual.

Trunk:
- *Size.*—12 cm in diameter at 90 cm above ground level.
- *Surface.*—Smooth.
- *Bark color.*—Grey 201D with shading of Grey 173D.
- *Lenticels.*—Length 1 cm, width 0.2 cm.
- *Lenticel color.*—Grey 201D.
- *Lenticel density.*—1 per $cm^2$.

Branches:
- 3-*year-old branch.*—4 cm in diameter, color Grey 201D.
- 2-*year-old branch.*—2 cm in diameter, color Grey 201D.
- 1-*year old branch.*—0.5 cm in diameter, color Greyed Orange 169D.
- *Lenticels.*—1 mm in diameter, elongated in shape, color Grey 201D.

Leaves:
- *Size.*—Length 10 cm to 13 cm, width 4 cm to 6 cm.
- *Texture.*—Somewhat leathery.
- *Form.*—Broadly lanceolate.
- *Base.*—Rounded.
- *Apex.*—Pointed.
- *Upper surface pubescence.*—None observed.
- *Lower surface pubescence.*—Finely pubescent.
- *Upper surface color.*—Green 137A.
- *Lower surface color.*—Green 138B.
- *Venation.*—Pinnate, 10 to 12 veins, mainly alternate.
- *Mid-vein.*—Red Purple 67A on most leaves.
- *Margin.*—Finely serrate.
- *Petiole length.*—35 mm to 40 mm.
- *Petiole width.*—1.5 mm to 2 mm.
- *Petiole upper color.*—Yellow Green 145 C.
- *Petiole lower color.*—Red 46 A at abscission layer becoming Red 47B at base of leaf to tip of leaf in the majority of leaves.
- *Petiole groove.*—Very fine, depth 0.1 mm.
- *Stipules.*—Very fine, at the base of the petiole on almost all leaves.
- *Stipule length.*—9 mm.
- *Stipule width.*—0.1 mm.
- *Stipule color.*—Yellow Green 144A.
- *Leaf glands.*—None observed.

Leaf buds:
- *Length.*—10 mm.
- *Width.*—10 mm.
- *Color.*—Red Purple 59A.
- *Placement on branch.*—Alternate, closely held to branch.
- *Internode distance.*—60 mm.

Spurs: Present on 4 year and older wood.
- *Length.*—20 mm.
- *Width.*—4 mm.
- *Color.*—Grey 201D.

Flowers:
- *Bloom period.*—Early to mid May in Northeastern Virginia.
- *Presentation.*—Showy.
- *Fragrance.*—Faint.
- *Fertility.*—Somewhat self-fertile, provides pollen for other varieties that bloom concurrently.
- *Pollination requirements.*—Pollen from another concurrently blooming variety.

Flowers at popcorn stage:
- *Pedicle.*—Length 3 cm, diameter 2 mm.
- *Pedicle color.*—Yellow Green 144A.
- *Bud.*—Length 15 mm, width 8 mm.
- *Bud color.*—White 155C petal color with a blush of Red Purple 63C.

Flowers at full bloom:
- *Corolla diameter.*—38 mm to 40 mm when fully open.
- *Numbers of flowers per cluster.*—5 to 6.
- *Petals.*—Arrangement: separate. Color: White 155C on upper surface, White 155A on lower surface. Petal number: average of 5. Petal Veins: upper color: White 155C, Lower Color: Red Purple 63C. Shape: rounded to slightly elongated. Margin: ruffled, can be curled inward at tip. Size: length 20 mm, width 15 mm. Texture: smooth. Petal apex: rounded. Petal base: broadly lanceolate.
- *Pedicel.*—Length 5 mm, width 3 mm, club shaped, color Yellow Green 141C.
- *Sepals.*—5 In number, wedge shaped, sharply pointed, length 5 mm, width 2 mm, color Yellow Green 145A.
- *Filaments.*—Length 7 mm, width 0.5 mm, color Green 141C, number 16 to 18.
- *Anthers.*—Length 5 mm, width 0.5 mm, color Yellow Green 149D.
- *Pistil.*—Length 8 mm to 10 mm, width 1 mm, color Yellow Green 149D.
- *Ovary.*—Length 4 mm, width 3 mm, color Green 141C.
- *Stigma.*—Width 2 mm, color Yellow Green 141D.
- *Style.*—Length — 9 mm, width 0.1 mm, color Yellow Green 141C.

Fruit:
- *Maturity when described.*—Firm ripe.
- *Date of picking.*—September $8^{th}$ on average in Northeastern Virginia.
- *Size.*—Axial diameter 75 mm, transverse diameter 85 mm.
- *Fruit weight (firm ripe).*—220 g to 240 g.
- *Form.*—Round to slightly flattened.
- *Cavity.*—Acuminate.
- *Basin.*—Symmetrical, abrupt at base, depth 20 mm, width 30 mm.
- *Calyx.*—Symmetrical, acuminate, depth 16 mm, width 30 mm.

Skin:

*Thickness*.—Medium thin, approximately 45 μm.

*Texture*.—Tender, medium glossy with medium cuticle wax.

*Tendency to crack*.—Can crack depending on weather and temperature. conditions.

*Lenticels*.—Very faint, round, size 0.001 mm in diameter, color white 155B.

*Skin color*.—Red 42B with faint striping of Red 42A over 60% to 80% of the surface.

*Ground color*.—Yellow Orange 20B.

Flesh:

*Aroma*.—Fragrant, sweet.

*Color*.—Yellow Orange 19C.

*Texture*.—Very crisp and juicy.

Core:

*Bundle area*.—Medium to ovate, cordate, symmetrical at base.

*Bundle*.—Inconspicuous, green, alternate above stamens.

*Carpillary area*.—Distinct, medium size.

*Calyx tube*.—Slightly urn shaped, open.

*Depth of tube to shoulder*.—16 mm.

*Styles*.—Distinct, pubescent.

*Stamens*.—One distinct whorl, small.

*Axillary cavity*.—Wanting.

*Seed cells*.—Walls thin, tough, length 17 mm, width 6 mm.

*Longitudinal section*.—Broadly ovate.

Seeds:

*Number perfect*.—10.

*Number in one cell*.—2.

*Length*.—7 mm.

*Breadth*.—3 mm.

*Form*.—Lanceolate.

*Color*.—Greyed Orange 178A.

Stem:

*Length*.—30 mm.

*Width*.—3 mm.

*Color*.—Grayed Red 178 A.

Use:

Shipping quality: Excellent for fresh and wholesale markets.

Keeping quality: Similar to 'Honeycrisp', averaging 0° F. in mid-winter.

Tree winter hardiness: Very winter hardy, similar to 'Honeycrisp', averaging 0° F. in midwinter.

Bud winter hardiness: Very winter hardy, similar to 'Honeycrisp'.

Drought tolerance: Similar to 'Honeycrisp'.

Disease resistance: Similar to 'Honeycrisp'.

I claim:

1. A new and distinct variety of apple tree, *Malus domestica*, substantially as herein shown and described, characterized by brighter red, more highly colored fruit than 'Honeycrisp' and bright red coloration of the petiole underside extending to the leaf midvein in a majority of leaves.

* * * * *